United States Patent
Feger et al.

(10) Patent No.: US 6,743,370 B1
(45) Date of Patent: Jun. 1, 2004

(54) CONDUCTIVE ELECTROLYTE FOR HIGH VOLTAGE CAPACITORS

(75) Inventors: Christopher Feger, Easley, SC (US); Timothy R. Marshall, Pickens, SC (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 10/155,526

(22) Filed: May 23, 2002

(51) Int. Cl.⁷ .............................................. H01G 9/035
(52) U.S. Cl. ...................... 252/62.2; 607/5; 361/506; 361/504
(58) Field of Search .................. 252/622; 361/506, 361/504; 407/5; 429/326, 339, 341, 343

(56) References Cited

U.S. PATENT DOCUMENTS

| | | | |
|---|---|---|---|
| 4,518,471 A | 5/1985 | Arora | |
| 4,525,249 A | 6/1985 | Arora | |
| 4,860,169 A | 8/1989 | Dapo | 361/506 |
| 5,131,388 A | 7/1992 | Pless et al. | |
| 5,496,481 A | 3/1996 | Liu | 252/62.2 |
| 5,522,851 A | 6/1996 | Fayram | |
| 5,715,133 A | 2/1998 | Harrington et al. | |
| 6,562,255 B1 * | 5/2003 | Feger | 252/62.2 |
| 6,587,329 B1 * | 7/2003 | Feger | 361/504 |

\* cited by examiner

Primary Examiner—C. Melissa Koslow
(74) Attorney, Agent, or Firm—Steven M. Mitchell

(57) ABSTRACT

The present invention is directed to a conductive electrolyte for use in high voltage electrolytic capacitors and to an electrolytic capacitor impregnated with the electrolyte of the present invention for use in an implantable cardioverter defibrillator (ICD). The electrolyte according to the present invention is composed of a two solvent mixture of ethylene glycol and a polar organic cosolvent from the group of 2-methoxyethanol, 2-ethoxyethanol, 2-butoxyethanol, hexyl alcohol, or di(ethylene glycol). Dissolved in this mixture is a combination of boric acid with either an aliphatic dicarboxylic acid of carbon chain length from eight to thirteen ($C_8$ to $C_{13}$) or a very long chain dicarboxylic acid, where the acid functional groups are separated by 34 carbons (referred to as "dimer acid"). The solution is then neutralized with an amine. A cathode depolarizer, or degassing agent, from the group of nitro-substituted aromatic compounds (nitroaromatics) can be added to reduce the amount of gas produced during capacitor life. Hypophosphorous acid and/or a colloidal suspension of silica in ethylene glycol may be added to enhance the life characteristics of the electrolyte, resulting in lower leakage currents and better voltage droop characteristics. The water content may be adjusted with deionized water to achieve a Karl Fischer titration (water content) measurement of 1.0–8.0% to achieve proper age characteristics.

31 Claims, No Drawings

CONDUCTIVE ELECTROLYTE FOR HIGH VOLTAGE CAPACITORS

This application is related to copending application Ser. No. 10/154,569, filed on May 23, 2002, now U.S. Pat. No. 6,587,329.

BACKGROUND OF THE INVENTION

1. Field of the Invention

The present invention is directed to a conductive electrolyte for high voltage electrolytic capacitors and to an electrolytic capacitor impregnated with the electrolyte of the present invention for use in an implantable cardioverter defibrillator (ICD).

2. Related Art

Compact, high voltage capacitors are utilized as energy storage reservoirs in many applications, including implantable medical devices. These capacitors are required to have a high energy density since it is desirable to minimize the overall size of the implanted device. This is particularly true of an Implantable Cardioverter Defibrillator (ICD), also referred to as an implantable defibrillator, since the high voltage capacitors used to deliver the defibrillation pulse can occupy as much as one third of the ICD volume.

Implantable Cardioverter Defibrillators, such as those disclosed in U.S. Pat. No. 5,131,388, incorporated herein by reference, typically use two electrolytic capacitors in series to achieve the desired high voltage for shock delivery. Electrolytic capacitors are used in ICDs because they have the most nearly ideal properties in terms of size, reliability and ability to withstand relatively high voltage. Conventionally, such electrolytic capacitors include an etched aluminum foil anode, an aluminum foil or film cathode, and an interposed kraft paper or fabric gauze separator impregnated with a solvent-based liquid electrolyte. While aluminum is the preferred metal for the anode plates, other metals such as tantalum, magnesium, titanium, niobium, zirconium and zinc may be used. A typical solvent-based liquid electrolyte may be a mixture of a weak acid and a salt of a weak acid, preferably a salt of the weak acid employed, in a polyhydroxy alcohol solvent. The electrolytic or ion-producing component of the electrolyte is the salt that is dissolved in the solvent. The entire laminate is rolled up into the form of a substantially cylindrical body, or wound roll, which is held together with adhesive tape and is encased, with the aid of suitable insulation, in an aluminum tube or canister. Connections to the anode and the cathode are made via tabs. Alternative flat constructions for aluminum electrolytic capacitors are also known, comprising a planar, layered, stack structure of electrode materials with separators interposed therebetween, such as those disclosed in the above-mentioned U.S. Pat. No. 5,131,388.

In ICDs, as in other applications where space is a critical design element, it is desirable to use capacitors with the greatest possible capacitance per unit volume. Since the capacitance of an electrolytic capacitor is provided by the anodes, a clear strategy for increasing the energy density in the capacitor is to minimize the volume taken up by paper and cathode and maximize the number of anodes. A multiple anode stack configuration requires fewer cathodes and paper spacers than a single anode configuration and thus reduces the size of the device. A multiple anode stack consists of a number of units consisting of a cathode, a paper spacer, two or more anodes, a paper spacer and a cathode, with neighboring units sharing the cathode between them. Energy storage density can be increased by using a multiple anode element, however, the drawback is that the equivalent series resistance, ESR, of the capacitor increases as the conduction path from cathode to anode becomes increasingly tortuous.

Typically, an implantable cardioverter defibrillator may utilize two 350 to 400 volt electrolytic capacitors in series to achieve a voltage of 700 to 800 volts. However, with the prospect for treatment of ventricular tachycardia with higher voltage pulses (up to 1000 volts), the need for a capacitor with a working voltage of greater than 400 volts becomes pronounced. There are numerous commercially available compositions of electrolyte for use in electrolytic capacitors than can conform to reasonable specifications, as long as the operating voltage of the capacitor remains at 400 volts or lower. However, once this limit is exceeded, the choices become more limited. There are relatively few electrolytes for this voltage regime, and the suitable electrolytes known in the art have several drawbacks, especially when used in a flat, stacked capacitor having a multiple anode configuration. First, glycol-based electrolytes suffer from relatively poor conductivity and ionic mobility. These electrolytes will produce a capacitor with significant energy loss due to a higher than acceptable equivalent series resistance (ESR). Second, γ-butyrolactone based electrolytes, which overcome the problems of ionic mobility, can not be used in conjunction with typical paper spacer pads. These require thicker, more expensive pads made out of manila fibers, and as a result of greater thickness, sharply reduce the energy density in flat stacked capacitor designs. Many high voltage electrolytes employ the use of very long chain dicarboxylic acids and large bases to achieve the necessary breakdown voltages, however, the resultant electrolytes have very low conductivities ($\leq 1$ mS/cm). For example, U.S. Pat. No. 4,860,169 to Dapo discloses an electrolytic capacitor for use in operation at voltages above 500 volts, produced by employing an electrolyte containing a straight chain saturated aliphatic dicarboxylic acid in which the carboxylic moieties are separated by at least 14 carbon atoms in a mixture of at least one polar organic solvent and water. The disclosed composition has a resistivity at 30° C. of 1280 Ω.cm (781 µS/cm), a pH of 9.68 and Scintillation voltage of 500V.

What is needed in the art is an electrolyte that provides acceptable breakdown characteristics with reasonable conductivity when impregnated in an electrolytic capacitor operating above 400 volts.

The present invention is directed to a conductive electrolyte for use in high voltage electrolytic capacitors and to an electrolytic capacitor impregnated with the electrolyte of the present invention for use in an implantable cardioverter defibrillator (ICD). The electrolyte according to the present invention is composed of a two solvent mixture of ethylene glycol and a polar organic cosolvent. Preferred cosolvents include alcohols, alkoxyalcohols and glycols, such as 2-methoxyethanol, 2-ethoxyethanol, 2-butoxyethanol, hexyl alcohol, or di(ethylene glycol). Dissolved in this mixture is a combination of boric acid with an aliphatic dicarboxylic acid, preferably either an aliphatic dicarboxylic acid of carbon chain length from eight to thirteen ($C_8$ to $C_{13}$), such as suberic, azelaic, sebacic, undecanedioic, dodecanedioic, or brassylic acid; or a very long chain dicarboxylic acid, where the acid functional groups are separated by 34 carbons (referred to as "dimer acid," as disclosed in U.S. Pat. No. 5,496,481, incorporated herein by reference). The solution is then neutralized with an amine, such as ammonia, dimethylamine, trimethylamine, diethylamine, triethylamine, ethanolamine, diethanolamine, triethanolamine, and diisoproplyethylamine. A cathode depolarizer, or degassing agent, from the group of nitro-substituted aromatic compounds (nitroaromatics), including nitrobenzene, nitrotoluene, nitrophenol, nitroacetophenone, nitrobenzyl alcohol, and nitroanisole, can be optionally added to reduce the amount of gas produced during capacitor life. Lastly, hypophosphorous acid and/or a colloidal suspension of silica in ethylene glycol can be optionally added to enhance the life characteristics of the electrolyte, resulting in lower leakage currents and better voltage droop characteristics. The water content can be adjusted with deionized water to achieve a Karl Fischer titration (water content) measurement of about 1.0% to about 8.0% to achieve proper age characteristics.

A representative composition according to the present invention that displays the desired properties is:

54.8% by weight ethylene glycol;

23.4% by weight 2-ethoxyethanol;

0.9% by weight boric acid;

5.3% by weight azelaic acid;

1.4% by weight ammonium hydroxide (30% in water);

0.9% by weight 3-nitroacetophenone;

9.7% by weight colloidal silica (20%) in ethylene glycol;

0.1% by weight hypophosphorous acid (50% in water); and 3.5% by weight water.

The electrolyte may be further neutralized with anhydrous ammonia to achieve a final pH of about 6.0 to about 10.0, preferably a pH of about 6.5 to about 7.5.

The electrolyte according to the present invention, when impregnated in an electrolytic capacitor, has a conductivity that is reasonable for use in a multiple anode stack configuration and a breakdown voltage of greater than 450 V.

DETAILED DESCRIPTION OF THE INVENTION

The present invention is directed to a high voltage, highly conductive electrolyte for electrolytic capacitors and to an electrolytic capacitor impregnated with the electrolyte of the present invention for use in an ICD. The electrolyte according to the present invention may be used in a capacitor operating at a working voltage greater than 400 V, allowing for the possibility of a defibrillator that has a paired voltage greater than 800 V.

Preferred embodiments of the present invention are now described. While specific configurations and arrangements are discussed, it should be understood that this is done for illustrative purposes only. A person skilled in the relevant art will recognize that other configurations and arrangements can be used without departing from the spirit and scope of the invention. It will be apparent to a person skilled in the relevant art that this invention can also be employed in a variety of other devices and applications.

The electrolyte according to the present invention is composed of a two solvent mixture of ethylene glycol and a polar organic cosolvent. Useful cosolvents include alcohols, alkoxyalcohols, and glycols, such as 2-methoxyethanol, 2-ethoxyethanol, 2-butoxyethanol, hexyl alcohol, di(ethylene glycol), propylene glycol, 2-(2-methoxyethoxy) ethanol, 2-(2-butoxyethoxy)ethanol, di(ethylene glycol) butyl ether and pentyl alcohol. Dissolved in this mixture is a combination of boric acid with an aliphatic dicarboxylic acid, preferably either an aliphatic dicarboxylic acid of carbon chain length from eight to thirteen ($C_8$ to $C_{13}$), such as suberic, azelaic, sebacic, undecanedioic, dodecanedioic, or brassylic acid; or a very long chain dicarboxylic acid, where the acid functional groups are separated by 34 carbons (referred to as "dimer acid," as disclosed in U.S. Pat. No. 5,496,481, incorporated herein by reference), such as is available from Sigma-Aldrich under the product number 432369 ("hydrogenated dimer acid"). The solution is then neutralized with an amine, such as ammonia, dimethylamine, trimethylamine, diethylamine, triethylamine, ethanolamine, diethanolamine, triethanolamine, diisopropylethylamine, methylamine and ethylamine. A cathode depolarizer, or degassing agent, from the group of nitro-substituted aromatic compounds (nitroaromatics), including nitrobenzene, nitrotoluene, nitrophenol, nitroacetophenone, nitrobenzyl alcohol, and nitroanisole, can be optionally added to reduce the amount of gas produced during capacitor life. Lastly, hypophosphorous acid and/or a colloidal suspension of silica in ethylene glycol can be optionally added to enhance the life characteristics of the electrolyte, resulting in lower leakage currents and better voltage droop characteristics. Phosphoric acid will produce similar results in small quantities. The water content may be adjusted with deionized water to achieve a Karl Fischer titration (water content) measurement of about 1.0% to about 8.0% to achieve proper age characteristics.

The electrolyte according to the present invention can be composed of the following ranges of components: about 40% to about 80% by weight ethylene glycol, no more than about 40% by weight of a polar organic cosolvent, no more than about 2% by weight boric acid, about 3% to about 6% by weight of either an aliphatic dicarboxylic acid of carbon chain length from eight to thirteen ($C_8$ to $C_{13}$) or a very long chain dicarboxylic acid where the acid functional groups are separated by 34 carbons, no more than about 5% by weight of an amine, 0% to about 2% by weight of a nitro-substituted aromatic compound as a degassing agent, 0% to about 10% by weight colloidal silica in ethylene glycol, 0% to about 2% by weight hypophosphorous acid and about 1% to about 10% by weight water.

A representative composition according to the present invention that displays the desired properties is: 54.8% by weight ethylene glycol, 23.4% by weight 2-ethoxyethanol, 0.9% by weight boric acid, 5.3% by weight azelaic acid, 1.4% by weight ammonium hydroxide (30% in water), 0.9% by weight 3-nitroacetophenone, 9.7% by weight colloidal silica (20%) in ethylene glycol, 0.1% by weight hypophosphorous acid (50% in water) and 3.5% by weight water. The electrolyte may be further neutralized with anhydrous ammonia to achieve a pH of about 6.0 to about 10.0, preferably a pH of about 6.5 to about 7.5. An exemplary electrolyte made according to this representative composition exhibited a conductivity (resistivity) at 37.0° C. of 3.45 mS/cm (290 Ω-cm), a minimum breakdown voltage of 460 V, an index refraction, $n_D$ (20° C.) of 1.4313, a viscosity of 33.8 cP at 37° C. and a Karl Fischer titration (water content) measurement of 5.2%. A capacitor impregnated with the electrolyte according to the present invention may have a working voltage of greater than 400 V, preferably about 400V to about 450V, allowing for the possibility of a defibrillator that has a paired voltage of greater than 800 V.

An electrolytic capacitor according to the present invention is constructed of anode and cathode layers, stacked with a paper insulator or spacer between each layer. The anode layer is composed of one or more anode foils stacked together without any paper spacer, to form a high energy density anode element. The anode and cathode layers are then grouped together in a parallel connection to produce sufficient capacitance for the intended function. This finished stack is inserted into a case with a geometry closely following the contour of the stack, and designed to minimize the space occupied inside the finished defibrillator. A wound roll configuration may also be used, as would be apparent to those skilled in the relevant art.

Aluminum foil is preferred for the anode and cathode layers, because of its ability to produce a sufficient quality oxide layer, its conductive properties, and its wide commercial availability. Other valve metal foils conventionally utilized in electrolytic capacitors could also be used, including titanium, tantalum, magnesium, niobium, zirconium and zinc. Preferably, a strip of unetched, high purity (99.99%) aluminum foil with high cubicity, wherein at least 85% of the crystalline aluminum structure is oriented in a normal position (i.e., a (1,0,0) orientation) relative to the surface of the foil, is used. Such foils are well-known in the art and are readily available from commercial sources known to those skilled in the art.

The anode foil may be etched in an aqueous halide based etch solution, typically a hydrochloric acid or sodium chloride solution, according to a conventional etch process; for example, U.S. Pat. No. 5,715,133 to Harrington et al. describes a suitable method of etching foil and is incorporated herein by reference in its entirety. The etch solution preferably consists of about 1.3% by weight sodium chloride, about 3.5% by weight sodium perchlorate, about 0.35% sodium persulfate, and deionized water. The etch solution preferably is heated to about 60° C. to about 95° C., more preferably 85° C. The foil is etched at a DC current density of about 0.01 A/cm$^2$ to about 0.30 A/cm$^2$, preferably 0.15 A/cm$^2$. A charge of about 20 coulombs/cm$^2$ to 100 coulombs/cm$^2$ is passed through the foil during the etching process, with about 50 coulombs/cm$^2$ preferred, which requires a time of about 2 minutes and 13 seconds to about 11 minutes and 7 seconds, with about 5 minutes and 30 seconds preferred.

The foil is then removed from the etch solution and rinsed in deionized water. Then the tunnels formed during the initial etch are widened, or enlarged, in a secondary etch solution, typically an aqueous based nitrate solution, preferably between about 1% to about 20% aluminum nitrate, more preferably between about 10% to about 14% aluminum nitrate, with less than about 1% free nitric acid. The etch tunnels are widened to an appropriate diameter by methods known to those in the art, such as that disclosed in U.S. Pat. Nos. 4,518,471 and 4,525,249, entirely incorporated herein by reference.

After the etch tunnels have been widened, the foil is again rinsed with deionized water and dried. Finally, a barrier oxide layer may be formed onto one or both surfaces of the metal foil by placing the foil into an electrolyte bath and applying a positive voltage to the metal foil and a negative voltage to the electrolyte. The barrier oxide layer provides a high resistance to current passing between the electrolyte and the metal foils in the finished capacitor, also referred to as the leakage current. A high leakage current can result in the poor performance and reliability of an electrolytic capacitor. In particular, a high leakage current results in greater amount of charge leaking out of the capacitor once it has been charged.

The formation process consists of applying a voltage to the foil through an electrolyte such as boric acid and water or other solutions familiar to those skilled in the art, resulting in the formation of an oxide on the surface of the anode foil. The preferred electrolyte for formation is a 100–1000 $\mu$S/cm, preferably 500 $\mu$S/cm, citric acid concentration. In the case of an aluminum anode foil, the formation process results in the formation of aluminum oxide ($Al_2O_3$) on the surface of the anode foil. The thickness of the oxide deposited or "formed" on the anode foil is proportional to the applied voltage, roughly 10 to 15 Angstroms per applied volt.

The etched and formed anode foils are cut and the capacitor assembled as discussed above. An electrolytic capacitor stack according to the present invention consists of a number of units of: cathode, a paper spacer, one or more anodes, a paper spacer and cathode; with neighboring units sharing the cathode between them.

The electrolyte of the present invention is then prepared. In one embodiment, initially, ethylene glycol is heated to 60° C. and azelaic acid and boric acid are added. The solution temperature is raised to 120° C. and held at about 120° C. to about 130° C. for one hour. The 60° C. temperature is chosen so that the acids (boric and azelaic) are soluble. However, these acids may be added at room temperature or at a higher temperature, provided that the solution is held at about 120° C. to about 130° C. for one hour after addition of the boric acid. The azelaic acid need not be added until after the one hour period, but before the solution cools to 60° C. The solution is then cooled to about 90° C. to about 100° C., preferably 90° C., and nitroacetophenone is added. The solution is allowed to cool to 60° C. and methoxyethanol is added. The temperature is lowered before adding the methoxyethanol to prevent volatilization of the methoxyethanol. A colloidal suspension of silica in ethylene glycol may then be added to enhance the life characteristics of the electrolyte. Alternatively, a colloidal suspension of silica in ethylene glycol may be added prior to the addition of methoxyethanol to achieve similar results. The solution is then cooled to below 30° C. and water, hypophosphorous acid and ammonium hydroxide are stirred in. Alternatively, hypophosphorous acid may be added prior to the addition of methoxyethanol to achieve similar results. The electrolyte may be further neutralized with anhydrous ammonia to achieve a final pH of about 6.0 to about 10.0, preferably a pH of about 6.5 to about 7.5.

The pre-assembled capacitor is then vacuum impregnated with the electrolyte of the present invention, by placing the capacitor in contact with the electrolyte and reducing the pressure to less than 50 cm Hg. The capacitor is held at this low pressure for 5 to 45 minutes with a preferred time of 15 minutes, and then pressure is restored, using the pressure to force the electrolyte mixture into the capacitor stack. The capacitor is then removed and placed in an oven at a temperature of about 65 EC to about 90 EC with a preferred temperature of 90 EC and a maximum oxygen atmospheric concentration of 2% for a period of about 2 hours to about 24 hours, with a preferred time of 4 hours. The capacitor is then aged in a normal manner by applying the working voltage to the capacitor, allowing the capacitor to reach this voltage, and then allowing the current to decrease. The electrolyte of the present invention allows for a working voltage of greater than 400 V, preferably about 400V to about 450V.

Electrolytic capacitors according to the present invention can be incorporated into implantable medical devices, such as implantable cardioverter defibrillators (ICDs), as would be apparent to one skilled in the art, as described in U.S. Pat. No. 5,522,851.

Having now generally described the invention, the same will be more readily understood through reference to the following examples which are provided by way of illustration, and are not intended to be limiting of the present invention.

EXAMPLES

Example 1

An electrolyte was prepared having the following formulation:

| | |
|---|---|
| Ethylene Glycol | 108.7 g |
| Azelaic Acid | 9.0 g |
| Boric Acid | 1.5 g |
| 3-Nitroacetophenone | 1.5 g |
| 2-Ethoxyedianol | 39.5 g |
| Ammonium Hydroxide | 2.4 g |
| Water | 6.0 g |

Initially, the ethylene glycol was heated to 60° C. and the azelaic acid and boric acid were added. The solution temperature was then raised to 120° C. and held at 120–130° C. for one hour. The solution was then cooled to 90° C. and the nitroacetophenone was added. The solution was further cooled to 50° C. and the ethoxyethanol was added. Finally, the solution was cooled to below 30° C. and the water and ammonium hydroxide were stirred in. The solution was further neutralized with a titration of anhydrous ammonia to a final pH (36.1° C.) of 7.0. The prepared electrolyte exhibited a Karl Fischer titration (water content) measurement of 5.75%, a conductivity of 3.3 mS/cm, an average viscosity of 10.14 cP, an index of refraction, $n_D(20°$ C.) of 1.4301 and an open cup scintillation voltage of 420 V at 37.0° C.

Slide capacitors composed of a 1"×5" glass slide sandwich consisting of either a single or a double layer anode interleaved between three 0.25 mil Kraft paper spacers and a conventional cathode (having a cathode-papers-anode(s)-papers-cathode arrangement) were impregnated with the prepared electrolyte. The single anode capacitor exhibited a capacitance of 3.2791 $\mu$F, an ESR of 20.34$\Omega$ and a breakdown voltage of 460 V. When employed in a dual-anode layer capacitor arrangement, the capacitor obtained a capacitance of 6.1736 $\mu$F and an ESR of 60.72$\Omega$.

Example 2

An electrolyte was prepared having the following formulation:

| | |
|---|---|
| Ethylene Glycol | 92.4 g |
| Azelaic Acid | 9.0 g |
| Boric Acid | 1.5 g |
| 3-Nitroacetophenone | 1.5 g |
| 2-Ethoxyethanol | 39.5 g |
| Colloidal silica in ethylene glycol | 16.3 g |
| Hypophosphorous acid | 0.2 g |
| Ammonium Hydroxide | 2.4 g |
| Water | 5.9 g |

Initially, the ethylene glycol was heated in a 200 mL tall form beaker to 60° C. and the azelaic acid and boric acid were added and allowed to dissolve. The. solution temperature was then raised to 120° C. and held at 120–135° C. for one hour. The solution was then cooled to 80° C. and the nitroacetophenone was added. The solution was allowed to cool to 60° C. and the ethoxyethanol was added. The solution was then cooled to 45° C. and the colloidal silica in ethylene glycol was added. Finally, the solution was cooled to below 30° C. and the water, hypophosphorous acid and ammonium hydroxide were stirred in. The solution was further neutralized with a titration of anhydrous ammonia to a final pH (34.9° C.) of 7.13. The prepared electrolyte exhibited a Karl Fischer titration (water content) measurement of 5.19%, a conductivity of 3.45 mS/cm, an average viscosity of 33.78 cP, an index of refraction, $n_D(20°$ C.) of 1.4313 and an open cup scintillation voltage of 460 V at 35.8° C.

Slide capacitors composed of a 1"×5" glass slide sandwich consisting of either a single or a double layer anode interleaved between three 0.25 mil Kraft paper spacers and a conventional cathode (having a cathode-papers-anode(s)-papers-cathode arrangement) were impregnated with the prepared electrolyte. The single anode capacitor exhibited a capacitance of 3.2431 $\mu$F, an ESR of 17.32$\Omega$ and a breakdown voltage of 460 V. When employed in a dual-anode layer capacitor arrangement, the capacitor obtained a capacitance of 5.7040 $\mu$F and an ESR of 85.48$\Omega$.

Example 3

An electrolyte was prepared having the following formulation:

| | |
|---|---|
| Ethylene Glycol | 543.5 g |
| Azelaic Acid | 30.0 g |
| Boric Acid | 3.0 g |
| o-Nitroanisole | 7.5 g |
| Hypophosphorous acid | 0.5 g |
| Ammonium Hydroxide | 12.1 g |
| Water | 30.0 g |

The ethylene glycol was placed in a 600 mL beaker and heated to 60° C. The azelaic acid and boric acid were added and the solution was heated to 120° C. and held at 120–130° C. for one hour. The solution was cooled to below 60° C. and the remaining components were added to form the electrolyte.

In a first experiment, 125.3 g of the prepared electrolyte were placed in a 200 mL tall form beaker and mixed thoroughly with 51.8 g of 2-butoxyethanol. The solution was further neutralized with anhydrous ammonia to a final pH (21.9° C.) of 7.40. A conductivity of 1.26 mS/cm was observed for the electrolyte.

In a second experiment, 125.3 g of the prepared electrolyte were placed in a 200 mL tall form beaker and mixed thoroughly with 44.7 g of hexylalcohol. The solution was further neutralized with anhydrous ammonia to a final pH (23.2° C.) of 8.71. A conductivity of 1.41 mS/cm was observed for the electrolyte.

In a third experiment, 125.3 g of the prepared electrolyte were placed in a 200 mL tall form beaker and mixed thoroughly with 71.0 g of di(ethylene glycol) butyl ether. The solution was further neutralized with anhydrous ammonia to a final pH (23.9° C.) of 7.09. A conductivity of 933 mS/cm was observed for the electrolyte.

In an additional experiment, the prepared electrolyte was impregnated into a multi-anode configuration flat-stacked capacitor, according to the present invention, consisting of 10 layers of three anodes. The capacitor was aged to 435 volts. The leakage current was 327.15 $\mu$A over one minute and 246.07 $\mu$A over 5 minutes. The capacitor obtained a capacitance of 173.51 $\mu$F with an ESR of 1.531$\Omega$, at 120 Hz. The prepared electrolyte was also impregnated into two multi-anode configuration flat-stacked capacitors, according to the present invention, consisting of 8 layers of four anodes. The capacitors were aged to 435 volts. The average leakage current was 305.43 µA over one minute and 225.08 µA over 5 minutes. The capacitors obtained an average capacitance of 179.98 µF with an ESR of 2.457Ω, at 120 Hz.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents. Additionally, all references cited herein, including journal articles or abstracts, published or corresponding U.S. or foreign patent applications, issued U.S. or foreign patents, or any other references, are each entirely incorporated by reference herein, including all data, tables, figures, and text presented in the cited references.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A conductive electrolyte for high voltage electrolytic capacitors, comprising:
   ethylene glycol;
   a polar organic solvent;
   boric acid;
   a dicarboxylic acid; and
   an amine.

2. An electrolyte according to claim 1, wherein said polar organic solvent is an alcohol, an alkoxyalcohol or a glycol.

3. An electrolyte according to claim 1, wherein said polar organic solvent is 2-methoxyethanol.

4. An electrolyte according to claim 1, wherein said polar organic solvent is 2-ethoxyethanol.

5. An electrolyte according to claim 1, wherein said polar organic solvent is 2-butoxyethanol.

6. An electrolyte according to claim 1, wherein said polar organic solvent is hexyl alcohol.

7. An electrolyte according to claim 1, wherein said polar organic solvent is di(ethylene glycol).

8. An electrolyte according to claim 1, wherein said dicarboxylic acid is an aliphatic dicarboxylic acid of carbon chain length from eight to thirteen ($C_8$ to $C_{13}$).

9. An electrolyte according to claim 8, wherein said aliphatic dicarboxylic acid is selected from the group consisting of: suberic acid, azelaic acid, sebacic acid, undecanedioic acid, dodecanedioic acid and brassylic acid.

10. An electrolyte according to claim 1, wherein said dicarboxylic acid is a dicarboxylic acid where the acid functional groups are separated by 34 carbons (dimer acid).

11. An electrolyte according to claim 1, wherein said amine is selected from the group consisting of: ammonia, dimethylamine, trimethylamine, diethylamine, triethylamine, ethanolamine, diethanolamine, triethanolamine and diisopropylethylamine.

12. An electrolyte according to claim 1, further comprising hypophosphorous acid.

13. An electrolyte according to claim 1, further comprising a colloidal suspension of silica in ethylene glycol.

14. An electrolyte according to claim 1, further comprising a cathode depolarizer.

15. An electrolyte according to claim 12, wherein said cathode depolarizer is a nitro-substitute aromatic compound.

16. An electrolyte according to claim 13, wherein said nitro-substituted aromatic compound is selected from the group consisting of: nitrobenzene, nitrotoluene, nitrophenol, nitroacetophenone, nitrobenzyl alcohol and nitroanisole.

17. An electrolyte according to claim 1, wherein said electrolytic capacitor has a working voltage of greater than 400 V.

18. A conductive electrolyte for high voltage electrolytic capacitors, comprising ethylene glycol, 2-ethoxyethanol, boric acid, azelaic acid, 3-nitroacetophenone, a colloidal silica in ethylene glycol, hypophosphorous acid, ammonium hydroxide and water.

19. An electrolyte according to claim 18, comprising about 40% to about 80% by weight ethylene glycol, no more than about 40% by weight 2-ethoxyethanol, no more than about 2% by weight boric acid, about 3% to about 6% by weight azelaic acid, no more than about 2% by weight 3-nitroacetophenone, no more than about 10% by weight of a colloidal silica in ethylene glycol, no more than about 2% by weight hypophosphorous acid, no more than about 5% by weight ammonium hydroxide and about 1% to about 10% by weight water.

20. An electrolyte according to claim 18, comprising 54.8% by weight ethylene glycol, 23.4% by weight 2-ethoxyethanol, 0.9% by weight boric acid, 5.3% by weight azelaic acid, 0.9% by weight 3-nitroacetophenone, 9.7% by weight colloidal silica (20%) in ethylene glycol, 0.1% by weight hypophosphorous acid (50% in water), 1.4% by weight ammonium hydroxide (30% in water) and 3.5% by weight water.

21. An electrolytic capacitor impregnated with the conductive electrolyte of claim 1.

22. An electrolytic capacitor impregnated with the conductive electrolyte of claim 18.

23. An implantable cardioverter defibrillator (ICD) comprising an electrolytic capacitor impregnated with the conductive electrolyte of claim 1.

24. An implantable cardioverter defibrillator (ICD) comprising an electrolytic capacitor impregnated with the conductive electrolyte of claim 18.

25. A method of making a conductive electrolyte for high voltage electrolytic capacitors, comprising:
   (1) mixing an ethylene glycol solvent, a polar organic solvent, boric acid, and a dicarboxylic acid to form a first solution; and
   (2) adding an amine to said solution to neutralize the pH of said solution.

26. A method according to claim 25 wherein step (1) is performed in the following order:
   (a) mixing an ethylene glycol solvent with boric acid and a dicarboxylic acid; and
   (b) adding a polar organic solvent.

27. A method according to claim 25 further comprising the step of:
   (3) adding a hypophosphorous acid.

28. A method according to claim 25 further comprising the step of:
(3) adding a colloidal suspension of silica in ethylene glycol.

29. A method according to claim 25 further comprising the step of:
(3) adding a cathode depolarizer.

30. A method according to claim 25, wherein step (2) achieves a final pH of said solution of about 6.0 to about 10.0.

31. A method according to claim 25, wherein step (2) achieves a final pH of said solution of about 6.5 to about 7.5.

* * * * *